US005785926A

United States Patent [19]

Seubert et al.

[11] Patent Number: 5,785,926
[45] Date of Patent: Jul. 28, 1998

[54] PRECISION SMALL VOLUME FLUID PROCESSING APPARATUS

[75] Inventors: Ronald Seubert, Issaquah; Maynard V. Olson, Seattle; Deirdre Meldrum, Seattle; Blake Hannaford, Seattle; Peter Wiktor, Seattle; Neal A. Friedman, Seattle; Donald B. Snow, Mercer Island; Ray Kraft, Seattle, all of Wash.

[73] Assignees: University of Washington, Seattle; GeneTools, Inc., Issaquah, both of Wash.

[21] Appl. No.: 531,215

[22] Filed: Sep. 19, 1995

[51] Int. Cl.$^6$ ............................................. B01L 3/02
[52] U.S. Cl. ................... 422/100; 73/864.11; 73/864.14; 73/864.22; 73/864.25; 422/82; 422/99; 435/287.1; 435/287.2; 435/289.1; 435/303.1
[58] Field of Search ............................. 422/100, 82, 99; 435/287.1, 287.2, 289.1, 303.1; 73/864.11, 864.14, 864.22, 864.24, 864.25

[56] References Cited

U.S. PATENT DOCUMENTS

| 4,429,583 | 2/1984 | Watanabe et al. | 73/864.12 |
|---|---|---|---|
| 4,517,160 | 5/1985 | Galle et al. | 422/65 |
| 4,659,677 | 4/1987 | Glover et al. | 436/174 |
| 4,877,745 | 10/1989 | Hayes et al. | |
| 4,927,603 | 5/1990 | Fischer et al. | 422/67 |
| 4,960,566 | 10/1990 | Mochida | 422/65 |
| 5,021,217 | 6/1991 | Oshikubo | 422/100 |
| 5,455,175 | 10/1995 | Wittwer | 435/286.1 |
| 5,544,535 | 8/1996 | Thomas | 422/100 |

OTHER PUBLICATIONS

MJ Research, Inc., Peltier Thermal Cyclers Product Brochure, date unknown.
IGN, Quad Flex and SPS Product Brochure, date unknown.
Beckman, Biomek 2000 Product Brochure, date unknown.
Stratagene, RoboCycler Gradient Temperature Cyclers Product Brochure, date unknown.
Packard, MultiProbe Product Brochure, date unknown.
Packard Today, MultiProbe Product Brochure, date unknown.
BioRobotics, BioPick Product Brochure, published 1995.
Tecan, Genesis Series Robotic Sample Processors Product Brochure, date unknown.
Tecan, MiniPrep Product Brochure, date unknown.
Tecan, TRAC Product Brochure, date unknown.
SLT, Elisa Product Brochure, date unknown.
EFD Dispense Valves Product, date unknown.
Robbins Scientific, Hydra 96 Product Brochure, date unknown.
Benetix, 'Q' Bot System Product Brochure, date unknown.
BioRobot 9600, Qiagen BioRobot 9600 Product Catalog, published 1995.
Techincon Instruments Corporation, The Technicon RA Systems Product Catalog, published 1988.
Wallace, Inc., Quadra 96 Product Catalog, date unknown.
Tomtec, Quadra 9600 Product Catalog, date unknown.
Tomtec, Quadra 96 Product Catalog, date unknown.
Rainin, EDP Plus Product Catalog, published Oct., 1989–1994.
Zymark, BenchMate II Workstations, date unknown.
Hamilton, Microlab AT Product Catalog, date unknown.
Hamilton Product Catalog, published Aug., 1990.
Kemble Instrument Company Limited, Kemtek 1000 Product Catalog, date unknown.

*Primary Examiner*—Jan Ludlow
*Attorney, Agent, or Firm*—Michael J. Folise

[57] ABSTRACT

A high precision, small volume fluid processing system employs open ended capillary tubes to meter, aliquot and mix small volumes of sample fluid and reagents. The system has an automatic mechanism for moving the capillary tubes as well as automated sub-systems for incubating and mixing fluids within the capillary tubes.

13 Claims, 6 Drawing Sheets

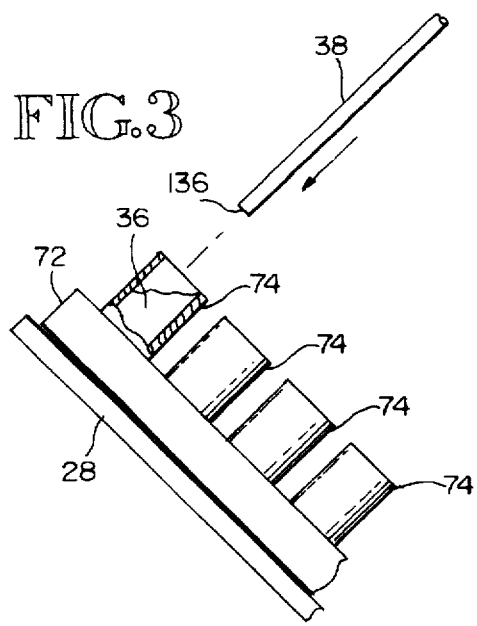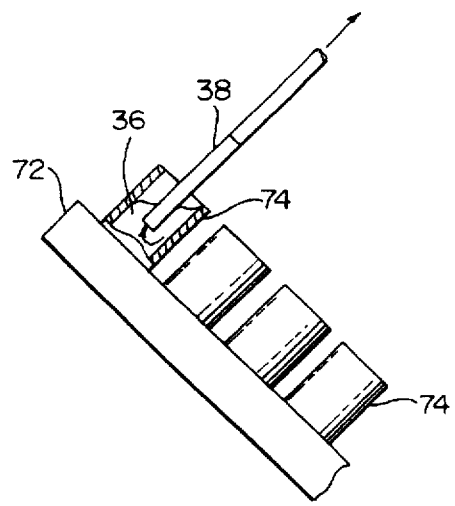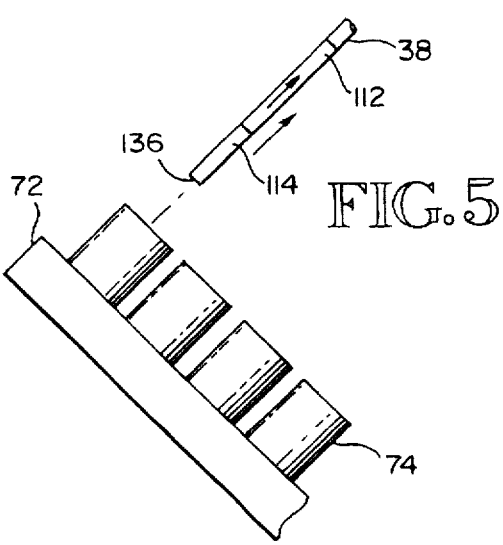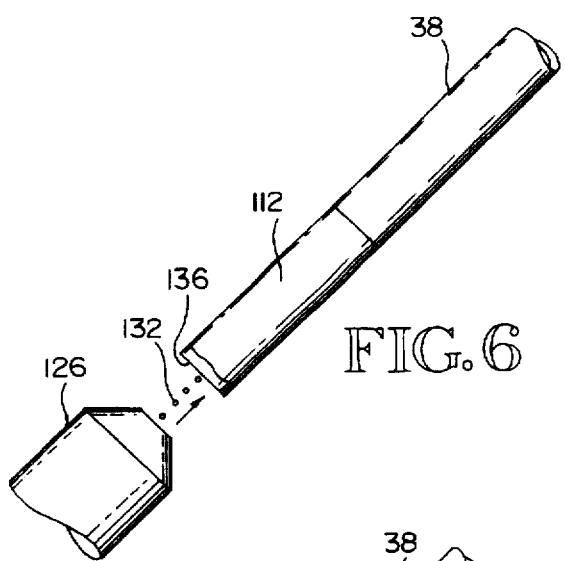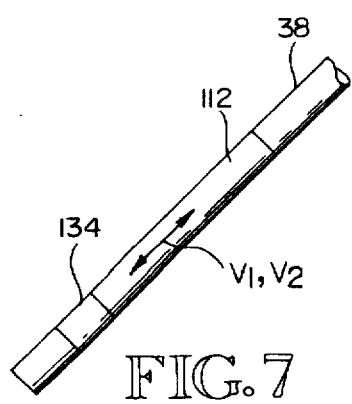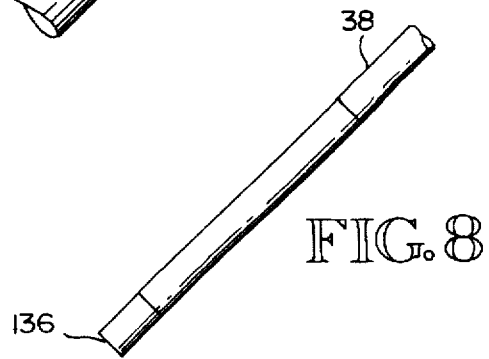

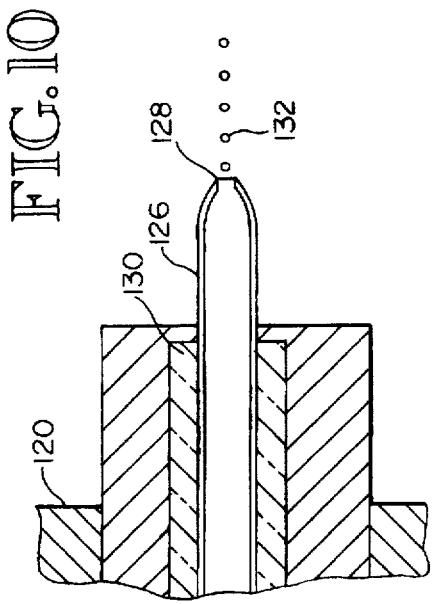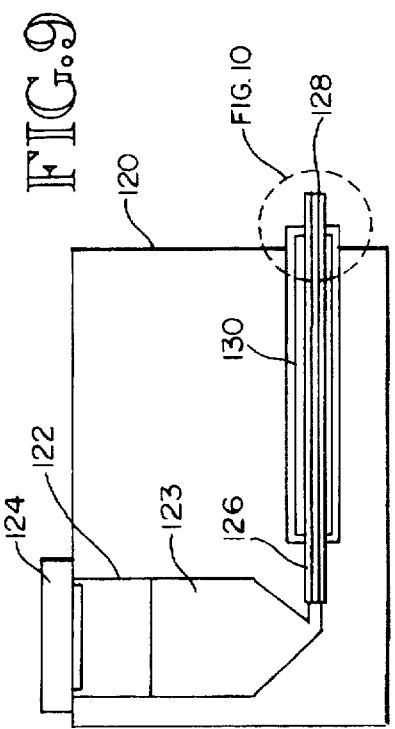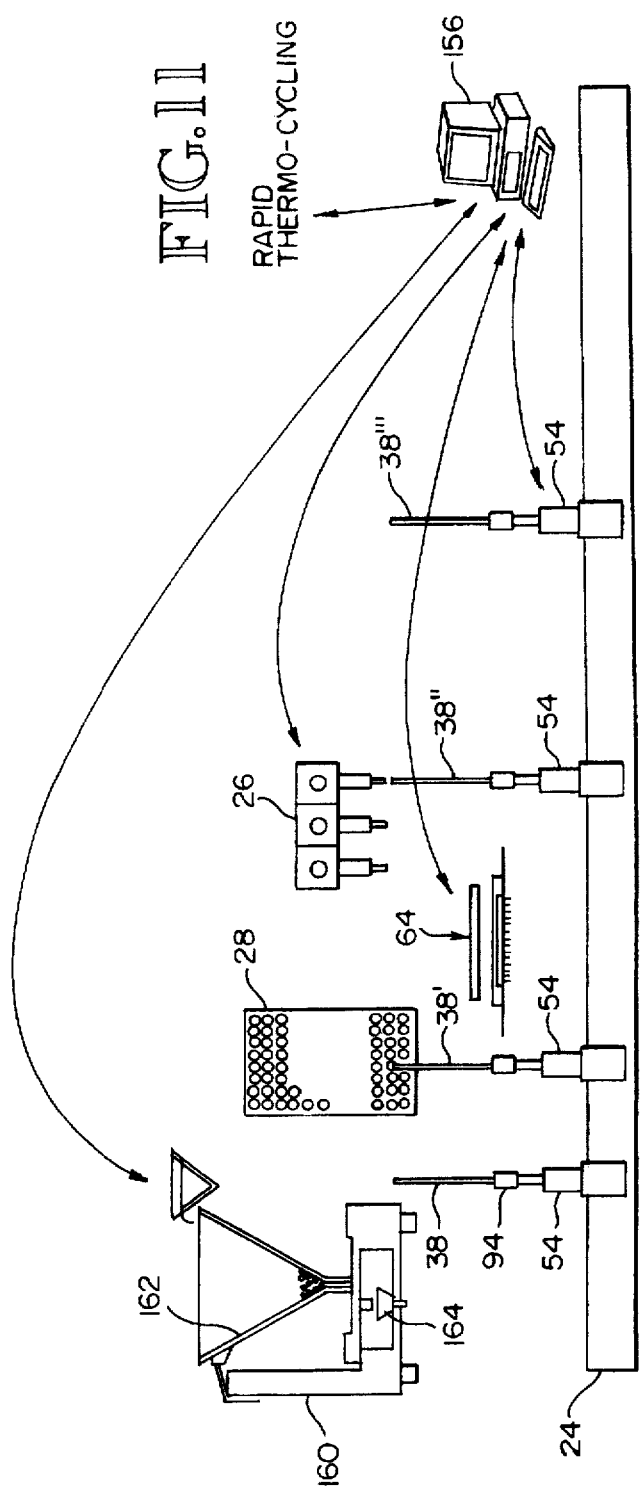

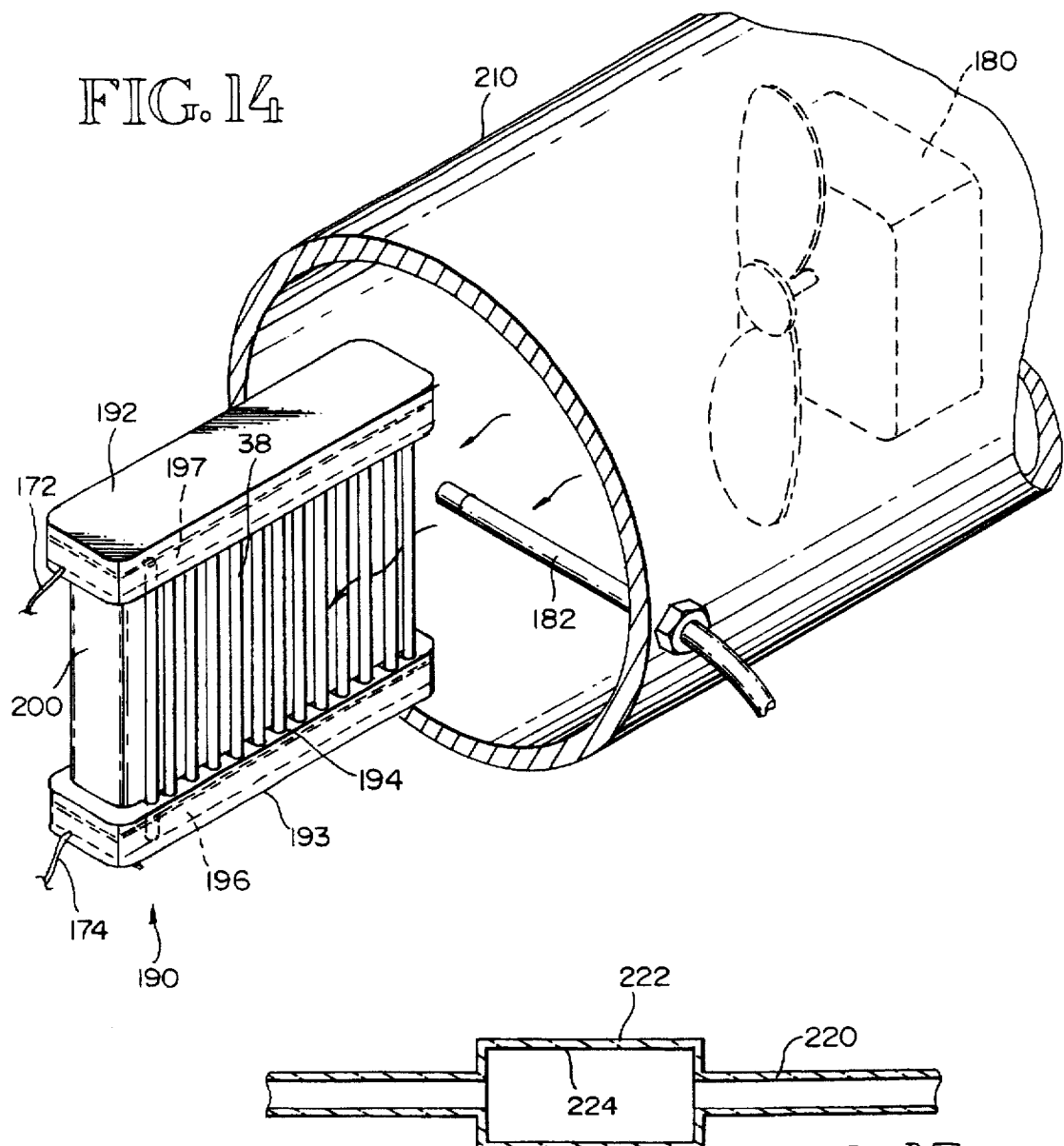
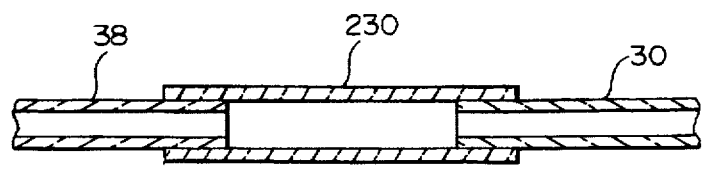

PRECISION SMALL VOLUME FLUID PROCESSING APPARATUS

TECHNICAL FIELD

The invention relates to methods and apparatus for precisely handling small volumes of fluids. More specifically, the invention relates to methods and apparatus for aliquoting and assaying biological fluid samples.

BACKGROUND OF THE INVENTION

Diagnostic and other biological assays often require systems for metering, dispensing and mixing reagents with sample fluids. The sample fluids may include, for example, patient samples, blood samples, or minute quantities of deoxygenated ribonucleic acid (hereinafter "DNA") sequences in a buffer fluid. Both manual and automated systems have been available for aliquoting the fluid samples, and assaying the samples with one or more reagents. Manual systems have historically included the glass capillary pipette, the micro pipette, precision syringes and weighing equipment. A variety of biological assays have been and continue to be conducted with manual equipment of the type described.

Relatively sophisticated microbiological assays including micro-enzyme linked immunosorbent sandwich assays (hereinafter "ELISA") can be satisfactorily, if tediously performed manually. The demands of modern antibody/antigen matching, histocompatibility typing, paternity testing, etc. on a vast scale has precipitated the development of various automated assay equipment to more quickly process large numbers of patient samples with various reagents. It is apparent that in order to perform a multiplicity of assays with a single patient sample, the amount of sample must be relatively large, or a small sample must be aliquoted into smaller divisions.

Recent advances in microbiology have provided the biotechnologist with increasingly sophisticated tools for examining genetic material. Restriction enzyme digestion and polymerase chain reaction (hereinafter "RED and PCR respectively") have provided geneticists with multiple DNA segments from a single sample for subsequent assaying. All of these advances have increased the need for sample handling and processing techniques which are beyond the ability of the heretofore manual pipetting and other standard laboratory techniques. As a result, the industry has proceeded with the development of highly automated equipment which can rapidly and repeatably handle relatively small quantities of patient samples.

The undertaking of the Human Genome Project exceeds the limits of current fluid sample handling and processing technology. The Human Genome Project is an attempt to map the entire human genetic code, nucleotide by nucleotide. The PCR and RED techniques presently available will therefore produce an extremely large numbers of nucleotide segments which must be assayed in a variety of different ways. In addition, current methods for producing the nucleotide segments are extremely expensive requiring the very wise use of the resultant sample. It is currently calculated that without further advancement in the state of the art, the cost of producing sufficient samples for laboratories around the world will be prohibitive without the development of techniques for handling much smaller samples and reagent volumes.

Therefore, a need exists for a high-precision, small volume fluid processing system which can aliquot and dispense fluid samples in extremely small volumes, react the samples with small quantities of reagents, and perform all of the other steps which may be necessary in a conventional assay. The system should also preferably be relatively highly automated so that the incidence of human error is reduced.

SUMMARY OF THE INVENTION

It is therefore an object of the present invention to provide a high precision, small volume fluid processing system which can precisely aliquot small volumes of a sample fluid.

It is a further object of the invention to provide a high-precision, small volume fluid processing system which can mix small aliquots of sample fluid with various discreet fluid reagents.

It is a further object of the present invention to achieve the above objects in a system which automatically aliquots the fluid sample, introduces appropriate reagents, mixes the sample and reagents, and incubates the same in preparation for gel electro phoresis.

It is yet a further object of the present invention to achieve the above objects in a system which can precisely and repeatably handle fluid volumes as small as 0.1 µl.

The invention achieves the objects, and other objects and advantages which will become apparent from the description which follows by providing a small volume fluid processing system employing at least one small volume capillary tube. A precision linear actuator connected to a computer controlled motor acts as a pneumatic piston to precisely inspire and expire one or more fluids into or out of the capillary in a predetermined sequence.

In a preferred embodiment, the fluid processing system can include a sample fluid station for containing an initial volume of sample material in a buffer solution or water, a reagent fluid dispensing device, monitoring equipment for determining the position of a fluid segment in the capillary tube and a mechanism for precisely positioning the fluid sample handling device in a reference plane with respect to the reagent fluid dispensing device in the sample fluid station. The sample fluid handling device can intake a precise volume of sample fluid from the sample fluid station, position itself adjacent to the reagent fluid dispensing device which can dispense an appropriate reagent into an open end of the capillary tube. The monitoring device can provide information to a computer or other management system to either advance or retard the precision linear actuator so as to move the fluids appropriately in the capillary tube. If two or more fluids have been received in the capillary tube, the linear actuator can be advanced and retarded with differential velocities so as to mix the fluids in the capillary tube. Very small volumes of fluids, as little as 0.1 µl can be handled with an accuracy of ±0.01 µl and similar repeatability if the precision linear actuator is driven by a computer controlled motor rotatably connected to a precision lead screw. The system described above may optionally contain a heating and cooling system for incubating the capillary tube in a controlled manner. The heating system can include a thin layer of highly resistive, transparent material on the outside of the tube which can be electrically excited so that a heat generating current flows therethrough. A fan can be used to cool the capillary tube while it is heated or afterwards to maintain a desired temperature or quickly cool the tube. The monitoring device for determining the position of a fluid segment in a capillary tube can be of the optical type including a light emitter/detector pair or array positioned in proximity to the capillary tube.

The sample fluid handling device can form a bubble or droplet of sample, reagent or other fluid on the open end of the tube having a known volume. By positioning a second capillary tube in alignment with and adjacent to the first capillary tube the droplet can be transferred from the first tube to the second tube by advancing the tubes towards one another until the droplet touches the second tube. Capillary action draws the droplet into the second tube in a repeatable manner. In this way, very small quantities of fluid can be transferred from one capillary to another. In an aliquoting method employing the processing system, the sample fluid handling device can inspirate aliquots of fluid sample separated by air gaps therebetween for a more precise dispensing of the aliquots into separate receiving capillary tubes.

BRIEF DESCRIPTION OF THE DRAWINGS

FIG. 3 is an enlarged, partial side elevational view of a capillary tube of the sample fluid handling device approaching a sample fluid station.

FIG. 4 is an enlarged, partial side elevational view similar to FIG. 3 showing the capillary tube inspiring a precise volume of sample fluid.

FIG. 5 is an enlarged, partial elevational view similar to FIG. 4 showing the sample fluid handling device being retracted from the sample fluid station.

FIG. 6 is an enlarged, partial elevational view of a reagent fluid dispensing device projecting reagent fluid droplets into the capillary tube.

FIG. 7 in an enlarged, elevational view of the capillary tube undergoing a mixing action.

FIG. 8 is a view similar to FIG. 7 showing the results of the mixing action.

FIG. 9 is a schematic representation of a piezo electric reagent dispenser.

FIG. 10 is an enlarged, partial sectional view of the circle area of FIG. 9.

FIG. 11 is a schematic representation of process steps employed by the system of the present invention.

FIG. 14 is an isometric, environmental view of a system for incubating a plurality of the capillary tubes in a controlled manner.

FIG. 15 in an enlarged, sectional view of a capillary tube employing a mixing compartment in a first alternate embodiment thereof.

FIG. 16 is a view similar to FIG. 15 of a second alternate embodiment of a capillary tube employing a mixing chamber.

DETAILED DESCRIPTION OF THE PREFERRED EMBODIMENTS

Figure 1:
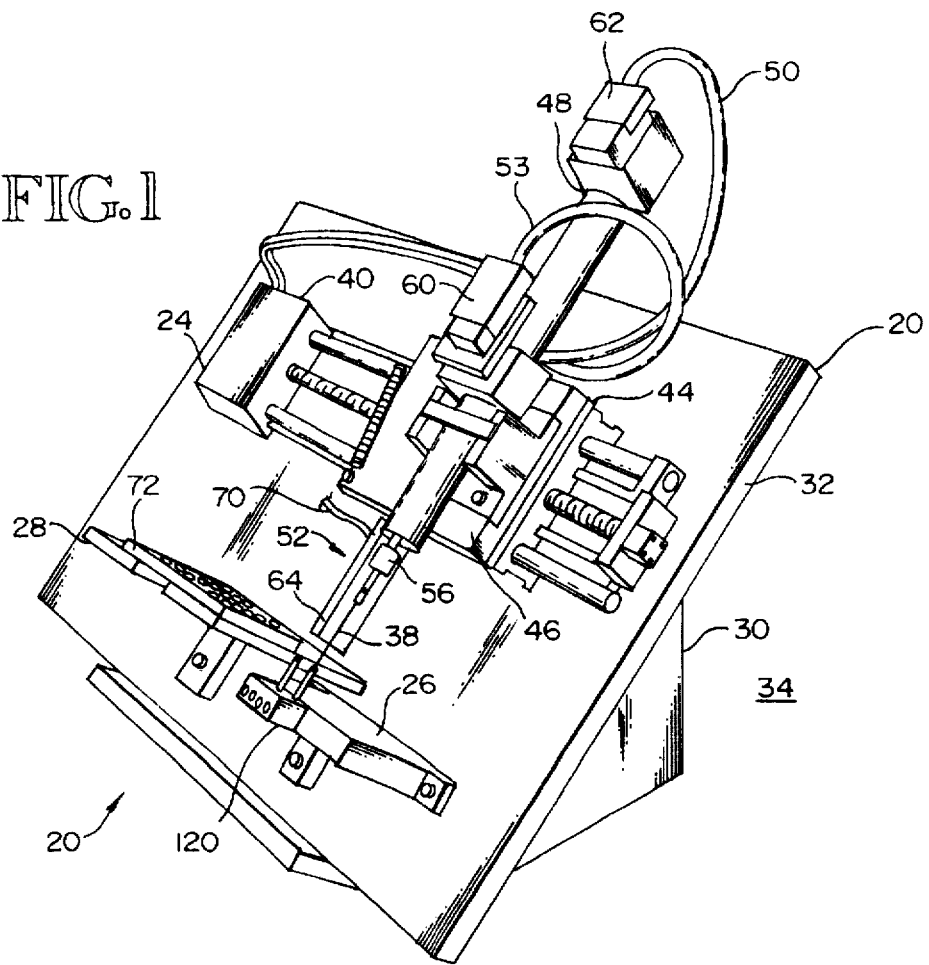
FIG. 1 is an isometric, environmental view of a high-precision, small volume fluid processing system of the present invention.
Figure 2:
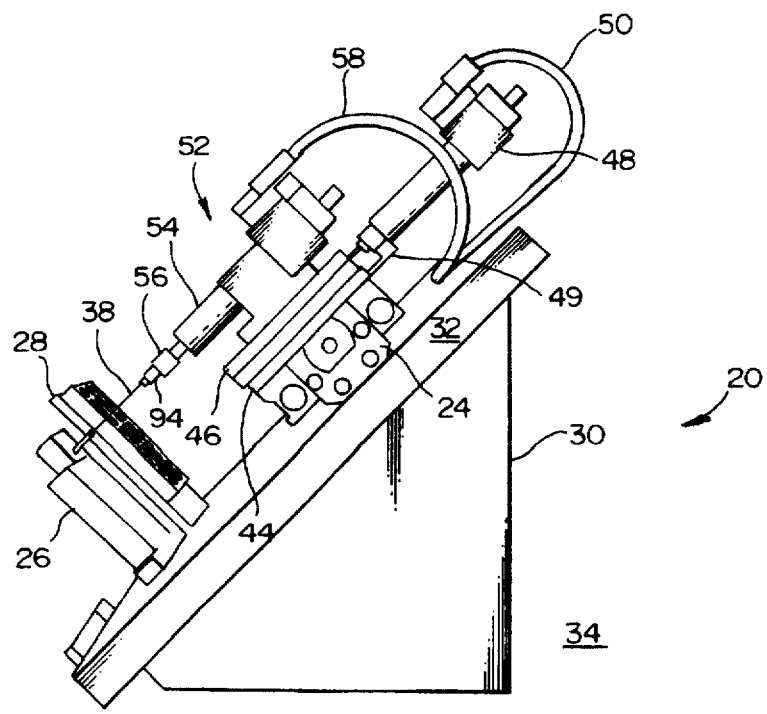
FIG. 2 is a side elevational view of the system shown in FIG. 1.

A high precision, small volume fluid processing system, in accordance with the principals of the invention, is generally indicated at reference numeral 20 in the Figures. With reference to FIGS. 1 and 2, the system includes a base 20, an X-Y axis positioning mechanism 24, a reagent dispensing station 26 and a sample station 28. The base includes a pair of supports 30 which position a base platform 32 at a 45° angle with respect to a support surface 34. The sample station 28 and reagent dispenser station 26 are positioned at 90° angles with respect to the platform 32 thus position the same at another 45° angle, with respect to the support surface 34. As shown in more detail in FIG. 3–5, the resulting spacial relationships positions the surface of a sample fluid 36 at approximately a 135° angle with respect to an open ended, hydrophilic capillary tube 38 for purposes which will be described in further detail below.

The X-Y positioning mechanism 24 includes a precision, screw actuated bed 40 for positioning an X axis stage 44 laterally with respect to the sample station 28 and reagent dispensing station 26. An appropriate precision screw actuated bed 40 is available from Applied Precision, Inc., Mercer Island, Wash., under the model number AP 1000. The X axis stage has a Y motion frame 46 adapted for transverse motion with respect thereto so as to position the capillary tube 38 axially with respect to the sample station 28 and reagent dispensing station 26. This is accomplished by mounting a stepper motor driven, computer controlled, precision linear actuator 48 on the X axis stage 44, while an axially reciprocable portion thereof 49 is mechanically connected to the Y motion frame 46. A computer or other suitable control device is connected to the actuator 48 by way of a control cable 50 in a manner to be described more fully below. An appropriate precision linear actuator 48 is available from Applied Precision, Inc., Mercer Island, Wash., under the brand name Nanomover™.

The Y motion frame 46 supports a sample fluid handling device generally indicated at reference numeral 52 which can precisely exspirate, and aspirate very small volumes of sample fluids, reagent fluids, etc. The device 52 includes a second, precision linear actuator 54, the open ended hydrophilic capillary tube 38 previously described, and an adapter mechanism 56 for fluidly interconnecting the capillary 38 with the actuator 54 such that an internal spindle of the actuator acts as a high precision, pneumatic piston for controlling the position of a fluid segments in the capillary tube. A second control cable 58 operatively interconnects the precision stepper motor of the actuator 54 with a computer or other appropriate control device in a manner similar to that described with respect to the first precision linear actuator 48. Both actuators contain relative or absolute position sensors 60, 62 which precisely determine the position of the stepper motor within the actuators, and thus the precise position of a fluid segment within the capillary tube 38.

Figure 13:
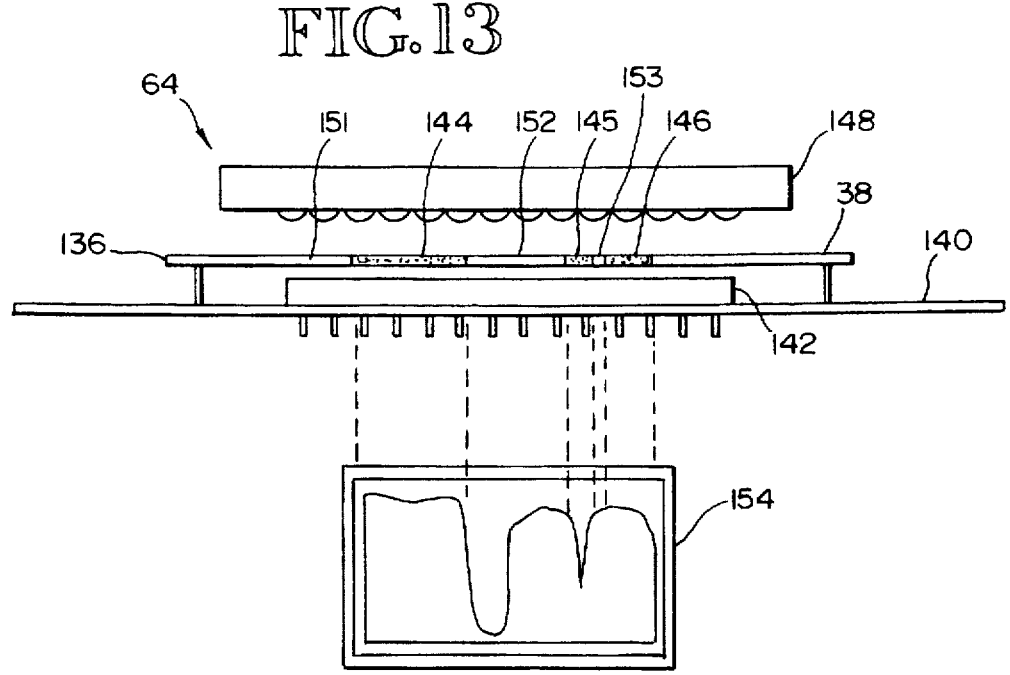
FIG. 13 is a schematic representation of an optical monitoring device for determining the position of fluid segments within the capillary tube.

Preferably, the sample fluid handling device 52 has mounted thereon an optical position determining sensor 64 one portion of which has been removed for clarity in FIG. 1 and which is illustrated in further detail, schematically in FIG. 13 to provide a fluid segment position feedback loop for directly determining the position of a fluid segment within the capillary tube 38. The sensor 64 is operatively interconnected with a computer or other appropriate control device through a third control cable 70.

The system described above permits very small, precise volumes of fluid sample and fluid reagents to be precisely metered, mixed, and incubated for advantageous application to PCR, enzyme restriction digestion, ELISA, DNA sequencing, and other microbiological assays and processing techniques. The system can accurately handle fluid samples as small as 0.1 μl with an accuracy of ±0.01 μl.

This technique is further illustrated in FIGS. 3–8 in which the sample station 28 has been adapted to receive a conventional, 96 well microtiter plate 72 having a plurality of microwells 74 containing a volume (typically 5 ml or less) of a fluid sample 36. The samples can be segments of DNA in a buffer solution from a single individual, or the like. As shown in FIG. 3, the capillary 38 is positioned laterally by the precision screw actuated bed 40 so as to be in alignment with one of the microwells 74 of the microtiter plate 72. The capillary tube is then advanced in the direction of the arrow under the urging of the first precision linear actuator 48 until it is in contact with a lower level of the fluid 36 as shown in FIG. 4. Sample fluid is then aspirated into the capillary tube 38 both by the natural capillary action of the tube, as well as by withdrawal of a spindle portion of the actuator functioning as a pneumatic piston as best seen with reference to FIG. 17.

Figure 17:
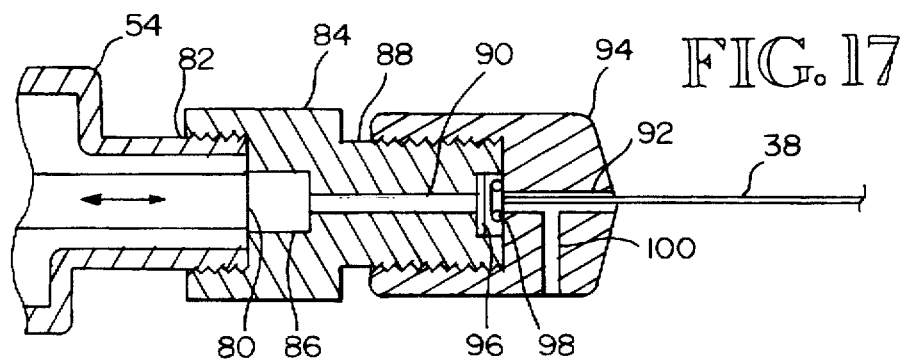
FIG. 17 is a partial, sectional elevational view of an adapter for fluidly connecting a capillary tube with a motor driven precision lead screw mechanism.

As shown in FIG. 17, the second, precision linear actuator 54 has a reciprocatable spindle portion 80 capable of precise axial movement in a manner well known to those of ordinary skill in the art. The actuator 54 has an extremely threaded end section 82 which has received thereon a cylindrical adapter 84 preferably manufactured from a nonreactive material such as stainless steel or heat treated aluminum. The adapter has a reduced diameter internal cavity 86 having a diameter of approximately 0.25 inch and an axial length of approximately 0.25 inch, and thus a volume of approximately 0.0128 cubic inches. The spindle portion 80 can protrude into this cavity so that the spindle and cavity form a precision pneumatic piston and cylinder. A forward, externally threaded end portion 88 of the adapter has a small diameter bore 90 therethrough for communication with an axial bore 92 of a threaded cap 94. The cap is preferably manufactured from Delrin, or another suitably nonreactive thermoplastic material. A small diameter washer 96, and "O" ring 98 are seated on an interface of the adaptor and cap so as to sealingly receive and seat the hydrophilic capillary tube 38 and to provide fluid communication between the capillary tube and bore 90. A radially directed vent 100 is in fluid communication with the axial bore 92 to relieve pressure within the cavity 86, bore 90 and bore 92 when the capillary tube is inserted into the cap 94.

With reference again to FIGS. 3, 9, and 8 it is now apparent that upon retracting the spindle portion 80 in FIG. 17, a controlled volume of sample fluid 36 will be drawn into the capillary tube 38 so as to form a sample fluid segment 112 as shown in FIG. 5 when the capillary tube is withdrawn from the microtiter plate 72. As further shown in FIG. 5, the position of the sample fluid segment 112 within the tube can be controlled by appropriate operation of the second precision linear actuator 54. In this way, an air gap 114 may or may not be created so as to form a physical barrier between the segment 112 and any additional sample fluid segments which may be inspired into the capillary tube 38 for subsequent aliquoting purposes as shall be described further herein below.

A suitable capillary tube 38 has a length of approximately 55 millimeters, a maximum interior volume of 5 µl. The capillary has an inner diameter of 0.0134 inches. Tubes of this type are available from Drummond Scientific Company, Broomall, Pa., under the trademark MICROCAPS, part no. 1-00-0050-55. Capillary tubes of this type are naturally hydrophilic when clean. Thus, upon inserting the capillary tube 38 into the sample fluid 36 as shown in FIG. 4, a small amount of fluid sample will be drawn into the capillary without any movement of the spindle portion 80 of the second precision linear actuator 54. In order to compensate for this "dead volume", a correction factor must be applied to the command signal sent to the second actuator through the cable 58. The dead volume $V_d$ follows the formula:

$$V_i = m\ V_d + b.$$

The dead volume $V_d$ may be calculated as: $V_d = X_{piston}$ $k + V_{d\text{-}min}$, where $X_{piston}$ represent the position of spindle portion 80, k represents a conversion factor from linear spindle position to displaced volume, and $V_{d\text{-}min}$ represents the minimum dead volume inherent in the system. In order to aspirate a desired volume of sample fluid 36, ($V_a$), the commanded aspiration is $V_{a\text{-}command} = V_a - V_1$.

Using five µl capillaries and the Nanomover™ brand linear actuator 52, adapter 56 and cap 94 described above, the quantities have the following values.

| Quantity | Value |
| --- | --- |
| m | $5.11 \times 10^{-3}$ |
| b | 0.057 µl |
| k | 31.7 µl/mm |
| $V_{d\text{-}min}$ | 28 µl |

This, for initial position of $X_{piston}=0$, the dead volume, $V_d$ is 28 µl and the initial take up due to capillary action is $V_i=0.2$ µl. Therefore, for commanded aspiration of 0.1 µl of sample fluid 36, this translated into a commanded aspiration of $V_{a\text{-}command} = -0.1$ µl—a negative aspiration command. That is, in order to compensate for the capillary action of hydrophilic tube 38, spindle portion 80 must move forward a distance equivalent to a volume of 0.1 µl. Larger desired volumes, $V_a$ will of course require positive aspiration commands.

It is possible to avoid the dead volume problem described above by using a hydrophobic capillary tube. The clean glass capillary can be made hydrophobic by coating the interior thereof with silicone oxide or another material well known to those of ordinary skill in the art. A suitable product is available from Sigma Chemical Co., St. Louis, Mo., under the trademark SIGMACOTE, part no. SL-2.

Once the desired volume of sample has been aspirated into the capillary tube 38 as shown in FIG. 3–5, the capillary tube 38 can be laterally moved into alignment with respect to the reagent dispensing station 26 to receive one or more appropriate reagents into the capillary tube for subsequent mixing with the fluid sample segment 112 of FIG. 5. The preferred embodiment of the invention employs piezo electric reagent dispensers 120 as shown in greater detail in FIGS. 9 and 10. An appropriate reagent dispenser of this type is disclosed by Hayes, et al. in U.S. Pat. No. 4,877,745 the disclosure of which is incorporated herein by reference. It is sufficient for the purposes of this disclosure to explain that the piezo electric reagent dispenser has a reagent well 122 closed by a removable cap 124. The well 122 contains an appropriate reagent 123 and is fluidly connected to a dispensing tube 126 having a dispensing orifice 128 at a free end thereof. The dispensing tube is concentrically surrounded by a piezo electric element 130 which when stimulated by an appropriate voltage generates a paristalic acoustic wave within the tube ejecting one or more droplets 132 of a reagent of known volume in a highly precise manner.

As shown in FIG. 6, the sample fluid segment 112 should be withdrawn a distance which corresponds to the volume of the droplets 132 and simultaneously with the expulsion thereof from the dispensing tube 126 so that the droplets do not encounter back pressure within the capillary tube. The result will be a second fluid segment 134 consisting exclusively of reagent fluid adjacent to the sample fluid segment 112. If an air gap 114 as shown in FIG. 5 is desired the series of segments within the capillary tube 38 shown in FIG. 7 will be as follows: reagent fluid segment 134, air gap segment 114, and the sample fluid segment 112. In either event, by oscillating the segments within the capillary tube 38 in opposite directions with differential velocities $V_1$, $V_2$ the fluids will mix within the capillary tube. To ensure adequate mixing, one of the velocities should be at least three times the other velocity, and the mixing should occur over 100 cycles at a frequency of three cycles per second. In a five µl capillary when 3 µl of fluids have been received, axial oscillation of the fluids of ±1.5 µl can occur without inadvertently aspirating the fluids from the free end of the capillary tube 38.

In order to accurately position the fluid segments with the capillary tube 38, an optical position measuring device 64 as shown in FIG. 1 is preferably provided although all of the sequencing steps described above can be and have performed in an open loop mode. The device 64 is further described schematically in FIG. 13 wherein a printed circuit board 140 supports a charge couple device 142 thereon for sensing the position of three exemplary fluid segments 144, 145, and 146 in the capillary tube 38. An array of light emitting diodes 148 illuminates the fluid segments within the capillary tube 38. Poto diodes detects the presence of light transmitted through air gaps 151, 152, and 153 and outputs this information to a charge coupled device which then transfers this information serially to a digital computer or other appropriate control device. As shown in the schematic representation at reference numeral 154, a graph of signal amplitude on the vertical axis versus segment position with respect to the free end 136 of the capillary tube 38 indicates not only the presence or absence of the fluid segments but their respective leading and trailing edges as well. Using standard interpolation techniques, resolutions of up to 50 nanometers of absolute position have been achieved by using a charge couple device array 42 manufactured by Sony under the model no. IFX503A. A development kit is included with this part which will enable those of ordinary skill in the art to execute the design shown in FIG. 13 without undue experimentation.

With reference to FIG. 11, it is seen that an appropriately programmed personal computer 156 employing conventional analog to digital controller modules (not shown) can be operatively interconnected with the precision screw actuated bed 40, first precision linear actuator 48, second precision linear actuator 54, piezo electric reagent dispensers 120 and optical position determining sensor 64 so as to comprise a fully automated precision small volume fluid processing apparatus. In addition, a capillary dispensing station 160 having a V shaped capillary trough 162 can be used to position individual blank capillary tubes in a receptacle 164. As will be apparent from examination of FIG. 17, it is possible for the second linear actuator 48 to advance the sample fluid handling device linearly towards the receptacle 164 (which is shown in elevational view for clarity) so as to insert a blank capillary tube 38 into the cap portion 94. The computer can then command the precision screw actuated bed 40 to position the second actuator 54 in alignment with the sample station 28 and receive a predetermined volume of sample as previously described. The optical position determining sensor 64 can then send position information to the computer 156 to confirm that the correct volume of sample fluid has been aspirated and positioned appropriately within the capillary tube 38. The computer can then command the bed 40, and actuator 48 to move the capillary tube 38 be moved into appropriate positioning 38" with respect to the reagent dispensing station 26 to receive one or more precisely predetermined volumes of reagent. Once the reagent (s) and fluid sample have been appropriately mixed within the capillary tube 38, the computer can command the capillary tube 38 to be moved to a new position 38'" for further processing.

Figure 12:
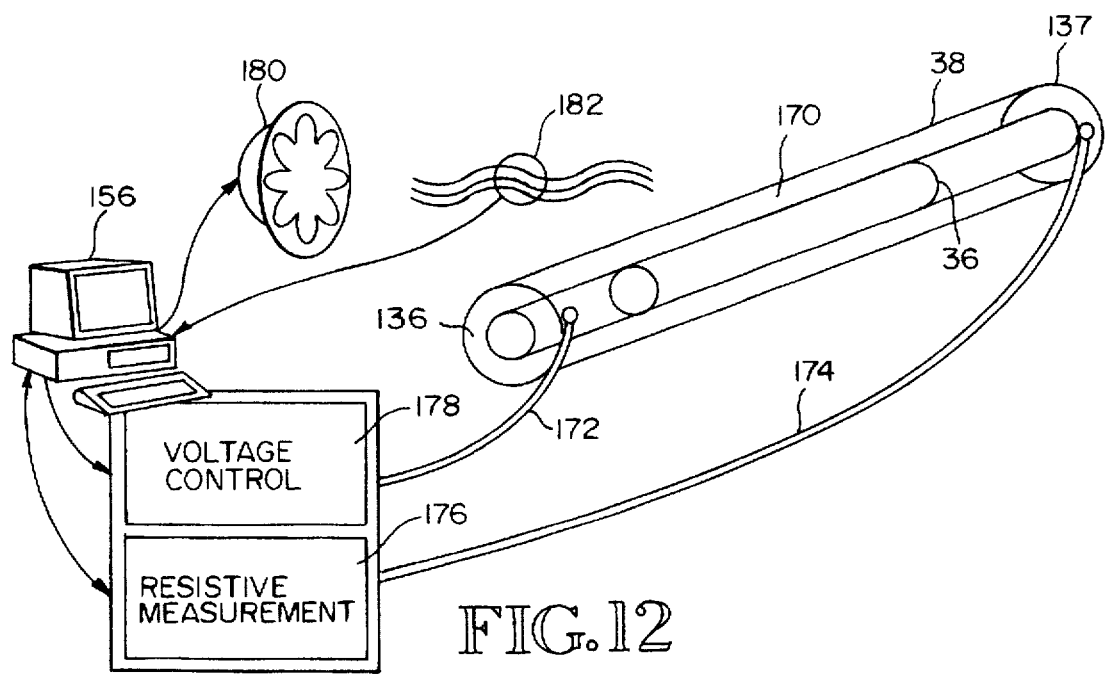
FIG. 12 is a schematic representation of an incubation system for the capillary tubes.

As shown in FIG. 12, further processing can include incubating the capillary tube 38 in an appropriate temperature controlled environment. This result can be achieved by providing a thin, substantially transparent, highly resistive coating 170 on the exterior of the capillary and connecting electrodes 172, 174 to an appropriate voltage source 178 which is in operative communication with the computer 156. Appropriate coating is indium tin oxide applied by the conventional vapor deposition techniques. It is known that the resistivity of a thin film of indium tin oxide changes with temperature, thus a continuous resistive measurement to be made by an electronically controlled Ohm meter 178 also operatively connected with the computer 156 can be used as a measurement of the tube temperature. A cooling fan 180 is preferably positioned advantageously with respect to the capillary tube 38 provide a constant air flow over the tube and a rapid cool down cycle when the voltage is no longer applied across the electrodes 172, 174. A conventional temperature sensor such as Thermistor type temperature sensitive resister 182 can also be preferably operatively interconnected with the computer to measure the temperature of the air flow exiting the fan 180.

FIG. 14 illustrates a preferred embodiment for implementing the incubation technique shown schematically in FIG. 12. Before the incubation step shown in FIG. 12 can proceed, both the free end 136 and an open mounting end 137 of the tube 38 should be heat sealed in the conventional manner. Once this has been done, a plurality of the sealed, capillary tubes 36 can be incubated by placing them in a holder, generally indicated at reference numeral 190 in FIG. 14. The holder includes opposed end caps 192, 193 having the electrodes 172, 174 therein and in communion with appropriately sized apertures 194 for receiving the capillary tubes 36. The exterior ends of the capillary tubes are preferably plated with chrome or another conductive material to make good electrical contact with a peripheral copper strip 196, 197 connected to the electrodes 172, 174. A spacer block 200 provides a mechanical support for the end caps to prevent the tubes from being crushed. In this preferred embodiment, the cooling fan 180 and Thermistor™ are contained in a plenum or duct 210 which directs the cooling air over and through the capillary tubes 36 for the purposes previously described.

As described above, the capillary tube 38 is preferably a hydrophilic tube. Moveover, as previously stated, the tube may be made hydrophobic by the introduction of appropriate materials. FIG. 15 shows an alternate preferred embodiment of a hydrophobic capillary tube 220 having an enlarged diameter mixing chamber 222. In this embodiment, the enlarged chamber in combination with an interior hydrophobic surface 224 increases turbulence in the tube during mixing and thus improves the mixing process. One technique for manufacturing such a tube is shown in FIG. 16 in another alternate embodiment in which two conventional sections of hydrophilic capillary tube 38 are joined in a spaced apart relationship by a larger diameter section 230 of a hydrophobic capillary tube section.

In the case of either embodiment shown in FIG. 15 or 16, these capillary tubes can be used in the same manner as shown with respect to the preferred, hydrophilic tube.

Finally, it should be noted that a capillary tube which is neither hydrophilic or hydrophobic can further be used.

Figure 18A:
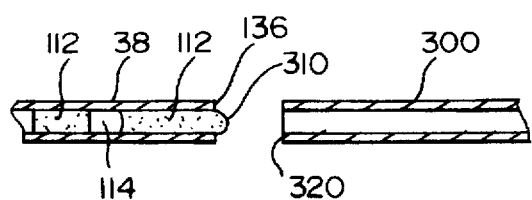
FIG. 18 is a schematic representation of a series of three steps for transferring a fluid droplet from a dispensing capillary to a receiving capillary in a method of the present invention.
Figure 18B:
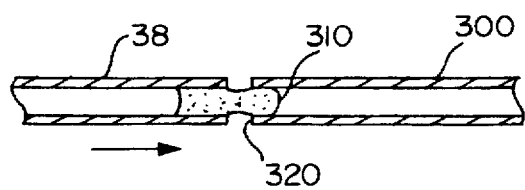
Figure 18C:
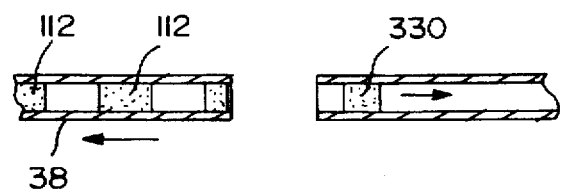

FIG. 18 illustrates an aliquoting method using the system shown in FIG. 10 wherein the reagent dispensing station 26 is provided with one or more hydrophilic receiving capillary 300 in place of the reagent dispensers 120. In this method as shown in FIG. 18(a) one or more segments 112 of sample fluid have been inspired into the capillary tube 38 and are separated by an air gap 114. By advancing the spindle portion 80 a desired amount a droplet 310 of known volume can be formed at the free end 136 of the capillary tube 38. As an example of the preferred embodiment given above, each step taken under computer control by the stepper motor of the actuator 54 corresponds to an increase in the size of the droplet 310 of 1.583 nanoliters. When an appropriately sized droplet is formed, the capillary tube 38 is advanced towards the receiving tube 300 by the first linear actuator 48 as shown in FIGS. 1 and 2. As shown in FIG. 18(b) as soon as the droplet contacts the free end 320 of the receiving capillary 300 the droplet 310 of known volume will be drawn into the receiving capillary 300 by capillary action. The steps shown in FIGS. 18(a) and 18(b) can be repeated until a sample fluid segment 330 having a volume equal to or less than the fluid segment 112 has been transferred. Droplets as small as 50 nanoliter increments have been transferred using this technique with the capillaries described. Once all of the sample fluid segment 112 has been transferred, the air gap 114 prevents the next sample fluid segment in capillary 38 from being inadvertently transferred. The capillary 38 may then be laterally moved to a second receiving capillary (not shown) and the process may be repeated. In this manner, the capillary tube 38 can be used to aliquot DNA samples into very small volumes, and distribute those volumes into separate receiving capillary tubes 300 which may then be individually processed with the appropriate as described herein above.

EXAMPLE I

The apparatus described above has been used to perform a restriction enzyme digest as described below.

In restriction enzyme digest (RED), a DNA sample is mixed with a "restriction enzyme" in a buffered solution and incubated. Each restriction enzyme will cleave that DNA at each site containing the sequence of base pairs specific to that enzyme. Restriction enzymes are sold commercially. An enzyme and DNA segment were chosen known to produce multiple cuts.

The DNA fragment sizes are determined by gel electrophoresis after the incubation. In this procedure, the (digested) DNA is placed on a gel (typically agarose) which is immersed in an electric field. The DNA will migrate through the gel at a rate determined by it's size: big pieces are slower.

First, an enzyme solution was prepared containing "Hind III" restriction enzyme, a buffer sold with the enzyme which is specific to that enzyme, sterile water, and an extra protein known as "BSA", according to the following recipe:
15 parts sterile, double distilled water
2 parts buffer
1 part BSA (2.5 mg/μl)
1 part enzyme (Hind III)

The BSA is necessary to keep the enzyme in the solution. Enzymes, like all proteins, tend to adhere to surfaces such as the inside of capillary tubes, test tubes, the pipette tips, and the reagent dispensers 120. The BSA is used as a sacrificial protein to occupy the adhesion sites and help keep the enzyme in solution. Gelatin and BSA are both commonly used for this purpose in micro-biology/genetics procedures.

The DNA chosen for this experiment was commercially prepared "Lambda" DNA, GibcoBRL part #25250-010, concentration 0.52 ug/μl. The enzyme chosen was "Hind III", GibcoBRL part #15207-012, concentration 10 U/μl, which comes with it's own specific buffer (GibcoBRL "React 2" buffer).

Starting with a clean, sterile container, 1 part DNA was added with 19 parts of the enzyme solution listed above. The resulting mixture was agitated, then incubated at 37C. for two hours. The volumes were reduced using the method of the invention by a factor of 10, to 0.1 μl of DNA and 1.9 μl of enzyme.

A large batch of the enzyme mix, 200 or 300 μl worth was mixed up with the excess and used to prime the reagent dispenser 120. The capillaries were then flame sealed with a butane torch prior to incubation.

Next the samples are removed from their capillary and placed on a 2%, agarose gel of the "high melt" variety—commonly known as "2% HMP agarose". The gel is exposed to an electric field, around 100–120 volts, for 15–20 minutes.

After electrophoreses, the gel is soaked in an Ethidium Bromide solution to stain the DNA, and examined under a UV light. DNA will show up as florescent bands.

All but the two smallest DNA bands could be identified. GibcoBRL note in their documentation these two bands are hard to distinguish because they are so much smaller than the largest fragment sizes, and this same caveat applies to their reference.

The bands from the samples matched the bands in the GibcoBRL reference, with the two smallest bands visible only faintly, even in the reference. The second smallest band was made more visible in the reference which was intentionally over-loaded a gel lane with excess DNA.

Other embodiments and variations of the invention are contemplated. Those of ordinary skill in the art will indeed conceive of other embodiments and variations of the invention upon review of this disclosure which are not herein described but are within the spirit of the invention. For example, it is contemplated that the receiving capillary 300 can be hydrophobic and can have an open mounting end (not shown) fluidly connected to a third precision linear actuator, similar to linear actuators 48, 54, by way of an additional adaptor 84 and cap 94. The third linear actuator can be coordinated with the first actuator which drives the dispensing capillary 38 in FIG. 18(a). In this way, the droplet 310 can be aspirated into the receiving capillary under positive control rather than by capillary action. Therefore, the invention is not to be limited by the above disclosure, but is to be determined in scope by the claims which follow.

We claim:

1. A high precision, small volume fluid processing system, comprising:

a sample fluid station;

a reagent fluid dispensing device;

a sample fluid handling device having a single open ended capillary tube fluidly connected to a precision linear actuator;

monitoring means for determining position information of ends of a fluid segment in the capillary tube;

positioning means for precisely positioning the fluid sample handling device in a reference plane with respect to the reagent fluid dispensing device and the sample fluid station; and, control means, operatively connected to the linear actuator and the positioning means, for positioning the capillary tube and operating the actuator to receive within the capillary tube both a precisely metered volume of sample fluid from the sample fluid station and at least one precisely metered volume of at least one reagent fluid from the reagent dispensing device.

2. The system of claim 1, wherein the linear actuator has a computer controllable motor rotatably connected to a precision lead screw, and wherein the capillary tube is removably and sealingly connected to the lead screw through an adaptor sized to removably receive the capillary tube in a friction fit.

3. The system of claim 2, wherein the adaptor has a housing defining a dead air volume and a cap portion having a stop ring and an "O" ring for sealingly receiving one of the open ends of the capillary tube, the cap portion further having a radially directed pressure relief vent.

4. The system of claim 1, wherein the monitoring means includes a light emitter/detector array having a plurality of sequentially arranged optical elements proximal to the capillary tube.

5. The system of claim 4, wherein the emitter/detector array has a plurality of charge coupled devices thereon.

6. The system of claim 1, wherein the capillary tube has an exterior, substantially transparent resistive coating thereon, and wherein the system includes controlled voltage generating means for causing a current to flow through the coating to heat the tube and wherein the system includes an air flow means, cooperatively interconnected with the controlled voltage generating means for incubating the capillary tube in a controlled manner.

7. The system of claim 6, wherein the coating is a layer of resistive material.

8. The system of claim 1, wherein the capillary tube has an enlarged diameter central interior portion defining a mixing chamber.

9. The system of claim 1, wherein the reagent fluid dispensing device is a ballistic fluid dispensing device.

10. The system of claim 1, wherein the reagent fluid dispensing device is a reagent fluid handling device having an open ended dispensing capillary tube fluidly connected to a precision linear actuator, wherein the linear actuator has a computer controllable stepper motor rotatably connected to a precision lead screw, and wherein the dispensing capillary tube is connected to the lead screw through an adaptor.

11. A high precision, small volume fluid aliquoting system, comprising:

a sample fluid station;

a receiving capillary tube having at least one open end;

a sample fluid handling device having a single aliquoting capillary tube having one end fluidly connected to a precision linear actuator, including control means for aspirating and handling a precisely metered volume of sample fluid through an open end of the aliquoting capillary tube; and, positioning means cooperatively coupled with the control means for precisely positioning the fluid sample handling device in a reference plane with respect to the sample fluid station and the receiving capillary tube so that the open ends of the receiving and aliquoting tubes can be precisely positioned adjacent one another for transferring a precise volume of sample fluid from the aliquoting capillary tube to the receiving capillary tube.

12. The system of claim 11, wherein the system includes a monitoring device for determining position information of ends of a fluid segment in the aliquoting capillary tube, and wherein the linear actuator has a computer controllable motor rotatably connected to a precision lead screw, and wherein the aliquoting capillary tube is connected to the lead screw through an adaptor.

13. The system of claim 12, wherein the adaptor has a housing defining a dead air volume and cap portion having a stop ring and an "O" ring for sealingly receiving one of the open ends of the aliquoting capillary tube, the cap portion further having a radially directed pressure relief vent.

* * * * *

UNITED STATES PATENT AND TRADEMARK OFFICE
CERTIFICATE OF CORRECTION

PATENT NO. : 5,785,926  
APPLICATION NO. : 08/531215  
DATED : July 28, 1998  
INVENTOR(S) : R. Seubert et al.

Page 1 of 1

It is certified that error appears in the above-identified patent and that said Letters Patent is hereby corrected as shown below:

| COLUMN | LINE | ERROR |
|---|---|---|
| 1 | 8 | insert in appropriate order<br><br>--STATEMENT OF GOVERNMENT LICENSE RIGHTS<br>This work was supported by NIH grant NCHGR HG00013. The U.S. Government may have certain rights in this invention.-- |

Signed and Sealed this

Fifteenth Day of May, 2007

JON W. DUDAS  
*Director of the United States Patent and Trademark Office*

UNITED STATES PATENT AND TRADEMARK OFFICE
CERTIFICATE OF CORRECTION

PATENT NO. : 5,785,926  Page 1 of 1
APPLICATION NO. : 08/531215
DATED : July 28, 1998
INVENTOR(S) : R. Seubert et al.

It is certified that error appears in the above-identified patent and that said Letters Patent is hereby corrected as shown below:

COLUMN  LINE  ERROR

1  8
should read

--STATEMENT OF GOVERNMENT LICENSE RIGHTS
This invention was made with U.S. Government support under grant No. NCHGR HG00013 awarded by the National Institutes of Health. The U.S. Government has certain rights in the invention.--

Signed and Sealed this

Ninth Day of February, 2010

David J. Kappos
*Director of the United States Patent and Trademark Office*